US008809275B2

(12) United States Patent
Servoss et al.

(10) Patent No.: US 8,809,275 B2
(45) Date of Patent: Aug. 19, 2014

(54) PEPTOIDS AND METHODS FOR TREATING ALZHEIMER'S DISEASE

(71) Applicants: The Board of Trustees of the University of Arkansas, Little Rock, AR (US); University of South Carolina, Columbia, SC (US)

(72) Inventors: Shannon Servoss, Fayetteville, AR (US); Melissa Moss, Columbia, SC (US)

(73) Assignees: The Board of Trustees of the University of Arkansas, Little Rock, AR (US); University of South Carolina, Columbia, SC (US)

( * ) Notice: Subject to any disclaimer, the term of this patent is extended or adjusted under 35 U.S.C. 154(b) by 0 days.

(21) Appl. No.: 13/656,198

(22) Filed: Oct. 19, 2012

(65) Prior Publication Data

US 2013/0102539 A1   Apr. 25, 2013

Related U.S. Application Data

(60) Provisional application No. 61/548,980, filed on Oct. 19, 2011.

(51) Int. Cl.
*C07K 7/06* (2006.01)
*C07K 7/08* (2006.01)
*A61K 38/00* (2006.01)

(52) U.S. Cl.
CPC .. *C07K 7/06* (2013.01); *A61K 38/00* (2013.01)
USPC ....... 514/17.8; 514/21.3; 514/21.4; 514/21.5; 514/21.6; 514/21.7; 530/325; 530/326; 530/327; 530/328

(58) Field of Classification Search
CPC ........... C07K 7/06; A61K 38/00; A61K 38/08
See application file for complete search history.

(56) References Cited

U.S. PATENT DOCUMENTS 7,632,816 B2 * 12/2009 Wisniewski et al. ........... 514/1.1

FOREIGN PATENT DOCUMENTS

WO    WO 2011/156003    12/2011

OTHER PUBLICATIONS

Rafii and Aisen 2009 "Recent Developments in alzheimer's disease therapeutics" BMC Medicine 7:7.*
Luo et al. 2013 "Inhibiting and reversing amyloid-b peptide 1-40 fibril formation with gramicidin S and engineered analogues" Chem Eur J 19:17338-17348.*
Adessi, C. et al., "Pharmacological profiles of peptide drug candidates for the treatment of Alzheimer's disease," (2003) *J. Biological Chemistry* 278(16):13905-13911.
Herrera J., "Peptoid-based therapeutics for Alzheimer's disease," Abstract presented at American Institute of Chemical Engineers 2009 Annual Meeting, Monday, Nov. 9, 2009.

(Continued)

*Primary Examiner* — Gregory S Emch
*Assistant Examiner* — Adam M Weidner
(74) *Attorney, Agent, or Firm* — Andrus Intellectual Property Law, LLP

(57) ABSTRACT

Provided herein are peptoids capable of inhibiting or reversing amyloid β (Aβ) fibril or plaque production. The peptoids form a helical structure with three monomers per helical turn and have at least two monomers with a side-chain having an arylalkyl group having the same chirality positioned such that the side-chains are on the same side of the peptoid. Also provided are methods of using the peptoids to inhibit or reverse aggregation of Aβ and methods of treating subjects with Alzheimer's disease (AD) or slowing the progression of AD.

12 Claims, 8 Drawing Sheets

(56) References Cited

OTHER PUBLICATIONS

Moss, M.A. et al., "The peptide KLVFF-K(6) promotes beta-amyloid(1-40) protofibril growth by association but does not alter protofibril effects on cellular reduction of 3-(4,5-dimethylthiazol-2-yl)-2,5-dipbenyltetrazolium bromide (MTT)," (2003) *Mol. Pharmacol.* (5):1160-1168.

Patch at al., "Versatile Oligo(N-substituted) glycines: The many roles of peptoids in drug discovery;" *Pseudo-Peptides in Drug Discovery*; Wiley-VCG Verlag (2004).

Soto-Ortega, D.D. et al., "Inhibition of amyloidβaggregation by coumarin analogs can be manipulated by functionalization of the aromatic center," (2011) *Bioorganic & Medicinal Chem.* 19:2596-2602.

Turner, J.P. et al., "Peptoids: A potential therapeutic agent against Alzheimer's disease," Abstract presented at American Institute of Chemical Engineers 2011 Annual Meeting, Wednesday, Oct. 19, 2011 (Available online Oct. 13, 2011).

Zuckermann, R.N. et al., "Efficient method for the preparation of peptoids [Oligo(N-substituted glycines)] by submonomer solid-phase synthesis," (1992) *J. Am. Chem. Soc.* 114:10646-10647.

\* cited by examiner

* Patch, J.A.; Kirshenbaum, K; Seurynck, S.L.; Zuckermann, R.N.; Barron, A.E., Versatiloligo (N-substituted) glycines: The many roles of peptoids in drug discover; Pseudo-Peptides in Drug Discovery; Wiley-VCG Verlag 2004

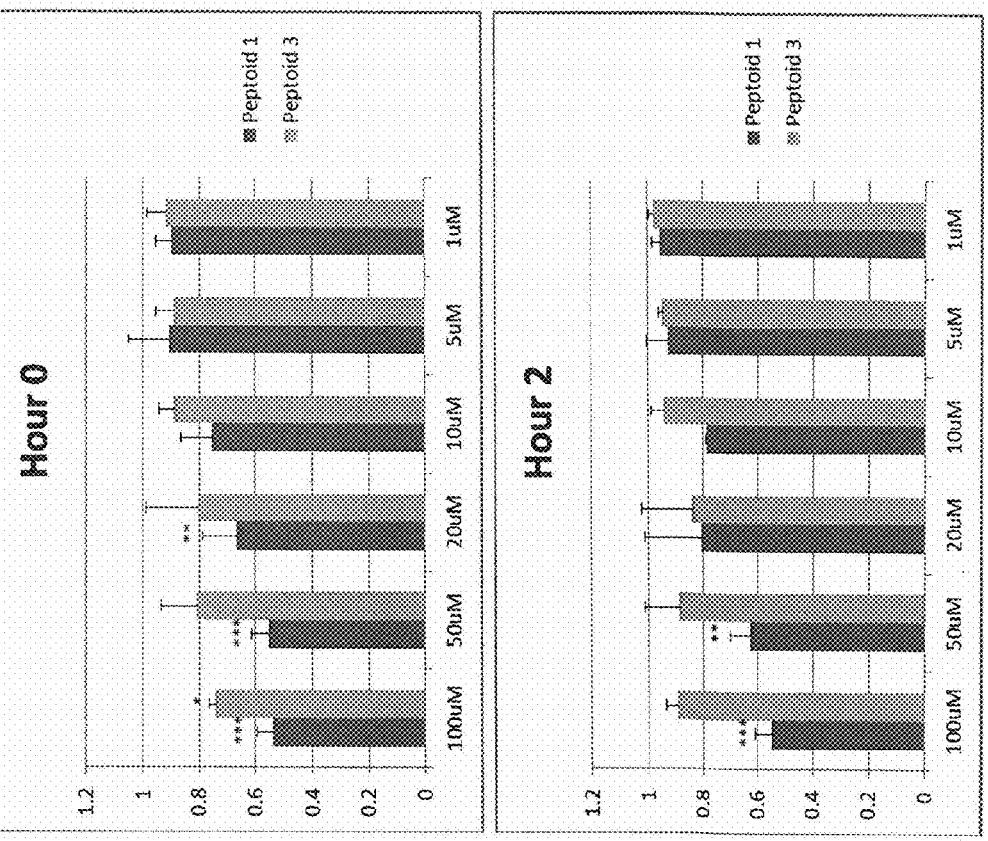

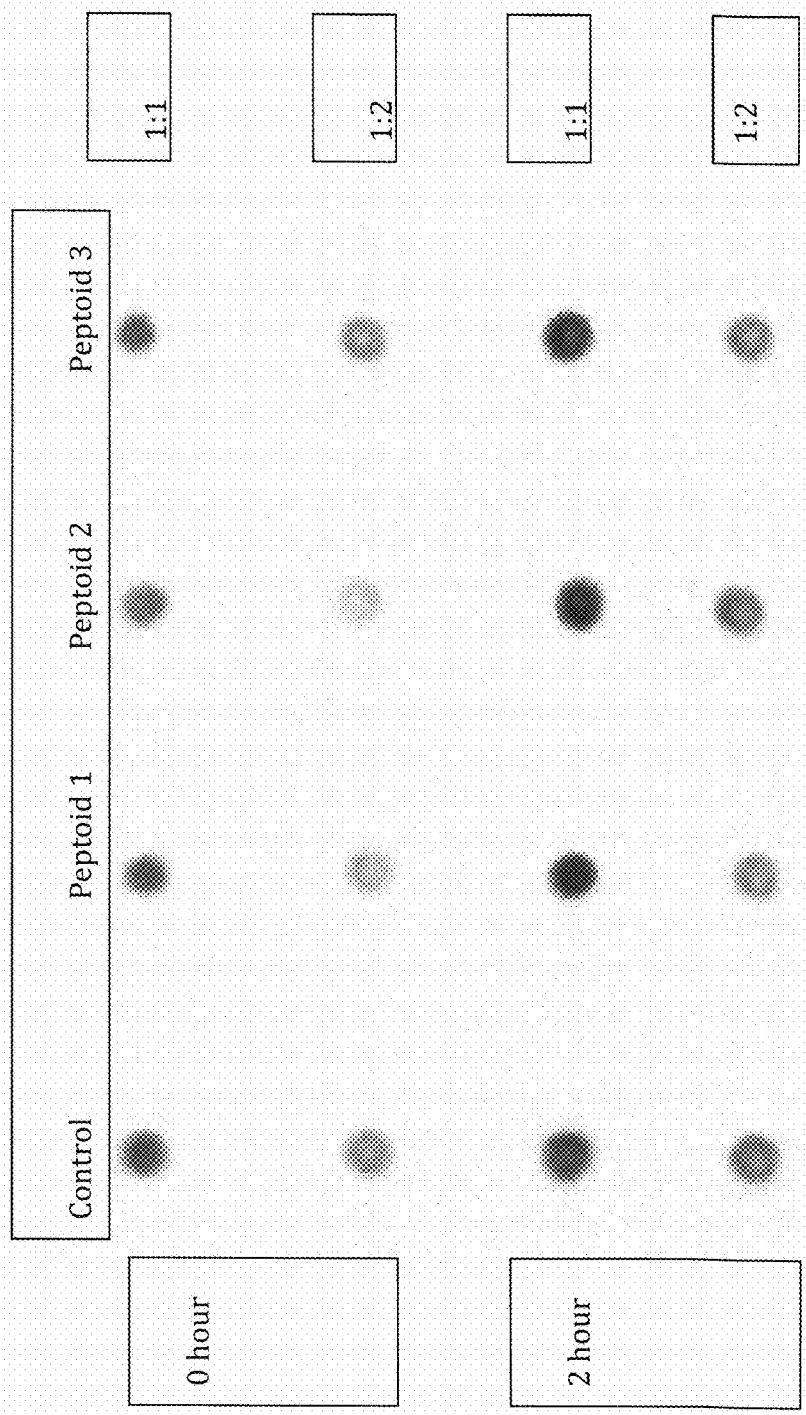

PEPTOIDS AND METHODS FOR TREATING ALZHEIMER'S DISEASE

CROSS-REFERENCE TO RELATED APPLICATIONS

This patent application claims the benefit of priority of U.S. Provisional Patent Application No. 61/548,980, filed Oct. 19, 2011, which is incorporated herein by reference in its entirety.

STATEMENT REGARDING FEDERALLY SPONSORED RESEARCH

This invention was made with United States government support awarded by the National Institutes of Health grant number 1P30RR031154-02 from the National Center for Research Resources. The United States may have certain rights in this invention.

INTRODUCTION

Alzheimer's disease (AD) is a devastating neurodegenerative disorder which is clinically characterized by deterioration of memory and cognitive function, progressive impairment of daily living activities, and several neuropsychiatric symptoms. AD is a genetically complex disease and only four genes have been established to either cause early-onset autosomal dominant AD with complete penetrance (APP, PSEN1 and PSEN2) or to increase susceptibility for late-onset AD with partial penetrance (APOE). All these four confirmed genes increase the absolute amyloid β (Aβ) levels or the ratios of Aβ 42 to Aβ 40, which enhances the aggregation of Aβ into neurotoxic assemblies. The aggregates eventually lead to formation of plaques in the brain and loss of nerve cells.

AD is the sixth leading cause of death in the United States. Currently there are no effective treatments available to stop or even significantly slow the progression of AD. Thus, development of a composition capable of slowing or stopping the aggregation of Aβ to stop or slow plaque development would be useful.

SUMMARY

Peptoids for inhibiting Aβ aggregation and slowing the progression of Alzheimer's disease are provided herein. The peptoids may be capable of reversing Aβ aggregation and plaque formation and thus may reverse or treat AD. The peptoids have the following formula:

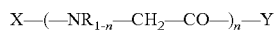

X—(—NR$_{1\text{-}n}$—CH$_2$—CO—)$_n$—Y wherein n is between 5 and 35, wherein X is H, wherein Y is selected from NH$_2$, H and OH, wherein R$_1$ of the peptoid is a branched or unbranched, saturated or unsaturated, substituted or unsubstituted C$_1$-C$_{10}$ alkyl group, wherein at least two R groups of R$_2$-R$_n$ of the peptoid comprise a branched arylalkyl group with either both (R) or (S) chiral centers, the aryl group may be substituted or unsubstituted, wherein the remaining R groups are branched or unbranched, substituted or unsubstituted, saturated or unsaturated, C$_1$-C$_{10}$ alky, C$_4$-C$_{10}$ aryl, or C$_4$-C$_{10}$ cycloalkyl groups, wherein the peptoid forms a helical structure with 3 monomers per turn such that the at least two R groups comprising the arylalkyl groups are positioned on the same face of the peptoid, wherein at least three and as many as 100% of the R groups with chiral centers have the same chirality.

In one aspect, peptoids having monomers in which every third monomer has an arylalkyl R group are provided.

In another aspect, the peptoids are the peptoids provided in FIG. 1.

In yet another aspect, pharmaceutical compositions comprising the peptoids described herein are provided, In still another aspect, methods of using the peptoids described herein to inhibit or reverse amyloid β aggregation by administering the composition to a subject in need of inhibition of amyloid β aggregation.

In still another aspect, methods of using the peptoids described herein to slow the progression of or reverse Alzheimer's disease by administering the peptoids to a subject in need of treatment for AD.

BRIEF DESCRIPTION OF THE DRAWINGS

FIG. 7 is a set of graphs showing that peptoid 1 and 3 can significantly inhibit Aβ aggregation in the in vitro thioflavin T assay. *, P<0.05. , P<0.01. *, P<0.001.

FIG. 8 is a photograph of a dot blot showing the ability of the peptoids to interfere with antibody binding to Aβ fibrils.

DETAILED DESCRIPTION

Peptoids for treating Alzheimer's disease (AD), inhibiting the progression of AD and inhibiting or reversing amyloid β (Aβ) aggregation are provided herein. Alzheimer's disease is a neurodegenerative disease that causes dementia in millions of patients worldwide and for which no effective treatment is currently available. AD is a result of chronic and vast accumulation of a toxic and insoluble Aβ peptide in the brain. The accumulation of Aβ causes loss of synapses, triggers neurofibrillary pathology and neural inflammation and results in neuronal loss. Aβ is an amphipathic peptide and is prone to self-aggregation. The reasons for Aβ accumulation are not clear, but once Aβ fibrils form Aβ plaques they attract further Aβ monomers. Thus once plaques are formed the progression of the disease is inevitable and no treatments currently exist.

Disclosed herein are peptoids (peptidomimetic oligomers) capable of inhibiting or even reversing Aβ fibril and plaque formation and either treating or inhibiting the progression of AD. Peptoids are similar to peptides as shown below. Peptoids allow for greater bioavailability than peptides since peptoid monomers are linked with an imide bond which is resistant to proteolytic degradation and the absence of hydrogen in amide groups in the backbone of the peptoids reduces compound polarity and improves membrane permeability. Use of peptoids may also reduce toxicity associated with peptide breakdown products. The peptoids described herein may be made and used using methods available to those skilled in the art. For example, see Zuckermann et al. Current Opinion in Molecular Therapeutics 11:299-307 (2009) and Ovadia et al. Bioorganic & Medicinal Chemistry 18:580-589

(2010) for information pertaining to the preparation and use of peptoids as therapeutics, the entire contents of which are incorporated herein in their entireties. The Examples below provide methods of making several of the peptoids provided herein.

Peptide:

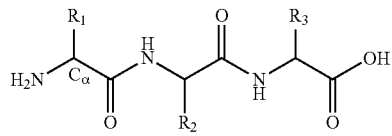

Peptoid:

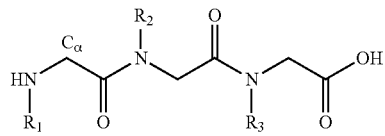

Figure 1:
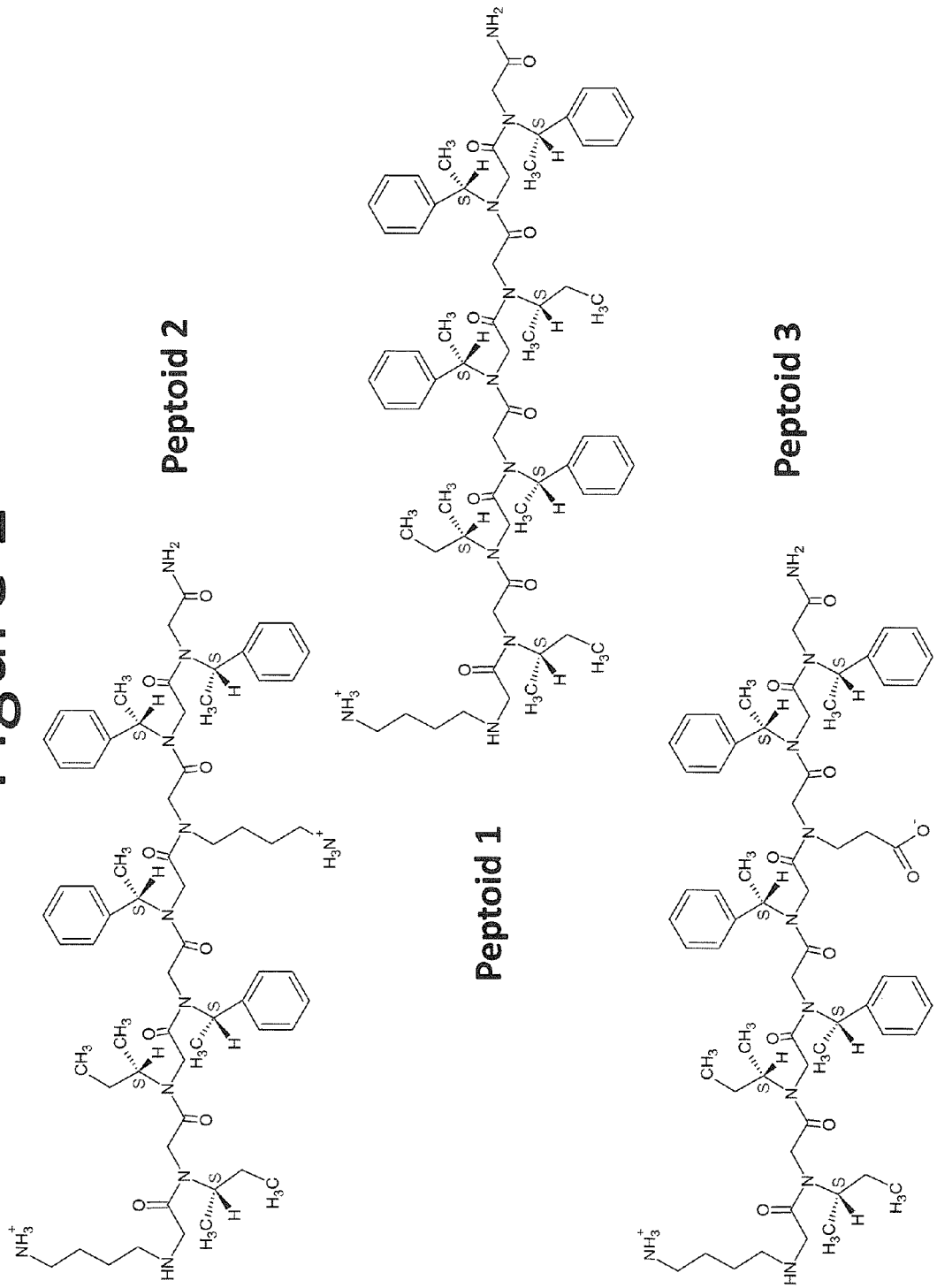
FIG. 1 is a depiction of the structure of three peptoids described herein.

The peptoids are designed to interact with Aβ and may be capable of reversing or inhibiting Aβ aggregation and plaque formation and thus may reverse or treat AD. The peptoids have the following general formula:

wherein n is between 5 and 35, wherein X is H, wherein Y is selected from $NH_2$, H and OH, wherein $R_1$ of the peptoid is a branched or unbranched, saturated or unsaturated, substituted or unsubstituted $C_1$-$C_{10}$ alkyl group, wherein at least two R groups of $R_2$-$R_n$ of the peptoid comprise a branched arylalkyl group with either both (R) or (S) chiral centers, the aryl group may be substituted or unsubstituted, wherein the remaining R groups are independently selected from branched or unbranched, substituted or unsubstituted, saturated or unsaturated, $C_1$-$C_{10}$ alky, $C_4$-$C_{10}$ aryl, or $C_4$-$C_{10}$ cycloalkyl groups, wherein the peptoid forms a helical structure with 3 monomers per turn such that the at least two R groups comprising the arylalkyl groups are positioned on the same face of the peptoid, wherein at least three and as many as 100% of the R groups with chiral centers have the same chirality. FIG. 1 shows the structures of three peptoids, namely peptoid 1, peptoid 2 and peptoid 3 which are made and used in the Examples.

As used herein, a monomer of the peptoid is a single (—$NR_{1-n}$—$CH_2$—CO—) group and n is the number of monomers. Suitably, the chirality of the monomers in the backbone of the peptoid are all the same. Each monomer includes a single R group which may also include a chiral center. Suitably, within a single peptoid all the chiral centers share the same chirality. Alternatively, the backbone chiral centers may be the same (i.e., all (R) or all (S)) and the R groups of each monomer may share the opposite chirality (i.e., (R) in the R side chains and (S) in the backbone). Alternatively only a portion of the R groups may share the same chirality. For example, three, four, five or more R groups may share the same chirality. Suitably, equal to or more than 50%, 55%, 60%, 65%, 70%, 75%, 80%, 85%, 90%, 95% of the R groups having a chiral center share the same chirality.

In some embodiments, the peptoid has at least five monomers (n=5). Suitably, the peptoids include 8, 10, 12, 15, 18, 20, 25, 30 or even 35 monomers. In one embodiment, the peptoid has an overall positive charge. In another embodiment, the peptoid is neutral or has a net negative charge. The N-terminal monomer has an R group ($R_1$) that may be selected from branched or unbranched, substituted or unsubstituted, saturated or unsaturated, $C_1$-$C_{10}$ alky, $C_4$-$C_{10}$ aryl, $C_4$-$C_{10}$ arylalkyl or $C_4$-$C_{10}$ cycloalkyl groups. In these peptoids, $R_1$ is suitably selected from an unbranched or branched, substituted or unsubstituted $C_1$-$C_6$ alkyl and if substituted the substitution is suitably nitrogen and suitably an amine. $R_1$ may have a positive charge or may be neutral. In the peptoids provided herein $R_1$ is 4-aminobutyl and the first monomer is N-(4-aminobutyl)glycine. Suitably, $R_1$ is a C2-C5 aminoalkyl. Suitably $R_1$ may be 3-aminopropyl, 2-aminoethyl or aminomethyl.

In the peptoids described herein, at least two and as many as two-thirds of the monomers have R groups that are arylalkyl groups with the same chirality (e.g. all of the arylalkyl groups have (S) or (R) chiral centers). Suitably the arylalkyl groups are arranged in the peptoid such that the peptoid has arylalkyl groups which are separated by two monomers. The peptoids form a helical structure with three monomers per helical turn of the peptoid such that the arylalkyl groups are stacked on one side of the helix in the peptoids. In some embodiments, the arylalkyl R groups represent up to one third of the total R groups and are spaced such that every third monomer in the peptoid is an arylalkyl. In other embodiments, up to two thirds of the monomers have arylalkyl R groups such that two out of every three R groups in the peptoid are arylalkyl groups. Suitably, the aryl alkyl groups are 1-phenylethyl as used in the Examples. Suitably additional arylalkyl groups may be used such as a phenylmethyl, phenylpropyl, phenylbutyl. The arylalkyl groups may include between 6 and 30 carbons. The arylalkyl may be branched or unbranched, substituted or unsubstituted and the alkyl portion may be saturated or unsaturated. Suitably the arylalkyl groups are unsubstituted or substituted with N, S or O. For example, in the peptoids provided in the Examples, $R_4$ and $R_7$ and $R_5$ and $R_8$ are arylalkyl groups such that the aryl groups are displayed on the same side of the peptoid when the peptoid adopts a helical structure with three monomers per turn of the helix. In the Examples the peptoids were made with (S) chiral centers, but (R) chiral centers are expected to perform similarly.

The remaining R groups may he branched or unbranched, substituted or unsubstituted, saturated or unsaturated $C_1$-$C_{10}$ alky, $C_4$-$C_{10}$ aryl or arylalkyl, or $C_4$-$C_{10}$ cycloalkyl groups. The remaining R groups ($R_2$, $R_3$ and $R_6$ in the peptoids provided in FIG. 1) are independently selected from branched or unbranched, substituted or unsubstituted, saturated or unsaturated, $C_1$-$C_{10}$ alkyl, aryl, heteroaryl, arylalkyl, cyclic, heterocyclic groups. Suitably, the peptoid has at least eight monomers, similar to those shown in FIG. 1, in which $R_2$, $R_3$ and $R_6$ are independently selected from 4-aminobutyl, 3-aminopropyl, 2-aminoethyl, or aminomethyl, pentyl, 2-butyl, butyl, propyl, ethyl, methyl, acetyl, acetylmethyl, acetylethyl, acetylpropyl, or acetylbutyl.

Without being limited by theory, the benzene rings of the arylalkyl groups are believed to interact with Aβ and block formation or growth of β-sheet aggregates. Thus a peptoid with side chains having benzene rings in every third position will form a helical structure with one face of the helix capable of interacting with Aβ to block aggregation or even reverse aggregation. Suitably a peptoid with monomers having two arylalkyl side chains followed by a third non-arylalkyl containing monomer would provide a peptoid having two faces capable of interacting with Aβ and blocking Aβ aggregate formation or growth.

Suitably, the peptoid is capable of inhibiting aggregation of Aβ by at least 75% in the thioflavin T assay as compared to a control untreated sample. Suitably the peptoid is capable of inhibiting aggregation of Aβ by at least 80%, 85%, 90%, 93%, 95%, 97%, 98%, 99% or more. Suitably the peptoid is able to accomplish the levels of inhibition dictated when added at an equimolar amount with the Aβ, or when added in excess, for example at a ratio of 2, 2.5, 3, 5, 7 or even 10 fold molar excess as compared to the Aβ. Suitably, the peptoids are capable of inhibiting Aβ aggregation by at least 10% as measured by a decrease in antibody binding to aggregated Aβ as compared to a control in which the Aβ monomers are allowed to aggregate. Suitably, the peptoids described herein are capable of inhibiting aggregation by 12%, 14%, 16%, 18%, 20% or even more.

The term "alkyl group" is intended to mean a group of atoms derived from an alkane by the removal of one hydrogen atom. Thus, the term includes straight or branched chain alkyl moieties including, for example, methyl, ethyl, propyl, isopropyl, butyl, tert-butyl, pentyl, hexyl, and the like. Preferred alkyl groups contain from 1 to about 14 carbon atoms ($C_{1-14}$ alkyl).

The term "aryl group" is intended to mean a group derived from an aromatic hydrocarbon by removal of a hydrogen from the aromatic system. Preferred aryl groups contain phenyl or substituted phenyl groups. Thus, the term "aryl" includes an aromatic carbocyclic radical having a single ring or two condensed rings. This term includes, for example, phenyl or naphthyl.

The term "heteroaryl" refers to aromatic ring systems of five or more atoms (e.g., five to ten atoms) of which at least one atom is selected from O, N and S, and includes for example furanyl, thiophenyl, pyridyl, indolyl, quinolyl and the like.

"Substituted" means that one or more of the hydrogen atoms bonded to carbon atoms in the chain or ring have been replaced with other substituents. Suitable substituents include monovalent hydrocarbon groups including alkyl groups such as methyl groups and monovalent heterogeneous groups including alkoxy groups such as methoxy groups. "Unsubstituted" means that the carbon chain or ring contains no other substituents other than carbon and hydrogen.

"Branched" means that the carbon chain is not simply a linear chain. "Unbranched" means that the carbon chain is a linear carbon chain.

"Saturated" means that the carbon chain or ring does not contain any double or triple bonds. "Unsaturated" means that the carbon chain or ring contains at least one double bond. An unsaturated carbon chain or ring may include more than one double bond.

The term "acyl or acetyl group" is intended to mean a group having the formula RCO—, wherein R is an alkyl group or an aryl group.

The term "alkenyl" refers to a straight or branched chain alkyl moiety having two or more carbon atoms (e.g., two to six carbon atoms, $C_{2-6}$ alkenyl) and having in addition one double bond, of either E or Z stereochemistry where applicable. This term would include, for example, vinyl, 1-propenyl, 1- and 2-butenyl, 2-methyl-2-propenyl, etc.

The term "cycloalkyl" refers to a saturated alicyclic moiety having three or more carbon atoms (e.g., from three to six carbon atoms) and which may be optionally benzofused at any available position. This term includes, for example, cyclopropyl, cyclobutyl, cyclopentyl, cyclohexyl, indanyl and tetrahydronaphthyl.

The term "heterocycloalkyl" refers to a saturated heterocyclic moiety having three or more carbon atoms (e.g., from three to six carbon atoms) and one or more heteroatom from the group N, O, S (or oxidized versions thereof) and which may be optionally benzofused at any available position. This term includes, for example, azetidinyl, pyrrolidinyl, tetrahydrofuranyl, piperidinyl, indolinyl and tetrahydroquinolinyl.

The term "cycloalkenyl" refers to an alicyclic moiety having three or more carbon atoms (e.g., from three to six carbon atoms) and having in addition one double bond. This term includes, for example, cyclopentenyl or cyclohexenyl.

The term "heterocycloalkenyl" refers to an alicyclic moiety having from three to six carbon atoms and one or more heteroatoms from the group N, O, S (or oxides thereof) and having in addition one double bond. This term includes, for example, dihydropyranyl.

The term "arylalkyl" refers to an alkyl group as defined above substituted with one or more aryl group as defined above. Suitably the arylalkyl group is an alkyl group substituted with one aryl group such as a phenylethyl group.

The term "halogen" means a halogen of the periodic table, such as fluorine, chlorine, bromine, or iodine.

The term "optionally substituted" means optionally substituted with one or more of the aforementioned groups (e.g., alkyl, aryl, heteroaryl, acyl, alkenyl, cycloalkyl, heterocycloalkyl, cycloalkenyl, heterocycloalkenyl, nitrogen, oxygen, sulfur or halogen), at any available position or positions.

Methods of making the compounds described herein are provided in the Examples. The compounds may be synthesized using conventional chemical technologies available to those skilled in the art. Salts of the compounds described herein are also provided. Suitably the salts are pharmaceutically acceptable. Acceptable salts of the compounds include, but are not limited to hydrochloride, hydrobromide, hydroiodide, nitrate, sulfate, bisulfate, phosphate, acid phosphate.

The compounds may be used to make pharmaceutical compositions. Pharmaceutical compositions comprising the peptoids described above and a pharmaceutically acceptable carrier are provided. A pharmaceutically acceptable carrier is any carrier suitable for in vivo administration. Examples of pharmaceutically acceptable carriers suitable for use in the composition include, but are not limited to, water, buffered solutions, glucose solutions, oil-based or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The composition may also be emulsified.

The peptoids provided herein may be used to make compositions capable of inhibiting Aβ aggregation both in vitro and in vivo and are capable of slowing the progression of AD in subjects suffering therefrom. In the methods, compositions comprising the peptoids described herein are administered to the subject in need of treatment. Suitably the compositions are formulated and administered such that the peptoids are able to cross the blood-brain barrier. Suitably the peptoids provided herein are able to treat or slow the progression of AD. Suitably, the peptoids provided herein are capable of reversing the progression of AD. Suitably, the peptoids are capable of breaking down or reversing aggregation of Aβ. Suitably the subjects are mammals, more suitably, humans.

Treatment of AD includes but is not limited to, prophylaxis of symptoms or indicators of the condition, reduction in disease severity or progression, or reversal, reduction or slowing in disease progression as compared to an untreated subject. The compositions described herein may be used to treat subjects in need of treatment for AD and may be used in combination with a second composition capable of inhibiting or slowing the progression of AD. The two compositions used together to treat a subject may be administered simultaneously or concomitantly or one before the other in any order. The two compositions may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

The compositions described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or via transmucosal absorption. Thus the compositions may be formulated as an ingestable, injectable, topical or suppository formulation. The compositions may also be delivered with in a liposomal or time-release vehicle. Suitably, the compositions are administered such that they are delivered or are able to cross the blood-brain barrier. Administration of the compositions to a subject appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the composition or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the composition of the invention and of a known agent, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the composition will inhibit progression of the condition by at least 10%, 20%, 30%, 40%, 50%, 60%, 70%, 80%, 90% or 100% compared to pre-treatment symptoms or progression of the disease if left untreated. It is specifically contemplated that pharmaceutical preparations and compositions may palliate or alleviate symptoms of the disease without providing a cure, or, in some embodiments, may be used to stop progression of the disease or disorder and in some cases may even reverse progression.

Suitable effective dosage amounts for administering the compositions may be determined by those of skill in the art, but typically range from about 1 microgram to about 100,000 micrograms per kilogram of body weight weekly, although they are typically about 1,000 micrograms or less per kilogram of body weight weekly. In some embodiments, the effective dosage amount ranges from about 10 to about 10,000 micrograms per kilogram of body weight weekly. In another embodiment, the effective dosage amount ranges from about 50 to about 5,000 micrograms per kilogram of body weight weekly. In another embodiment, the effective dosage amount ranges from about 75 to about 1,000 micrograms per kilogram of body weight weekly. The effective dosage amounts described herein refer to total amounts administered, that is, if more than one composition is administered, the effective dosage amounts correspond to the total amount administered. The composition can be administered as a single dose or as divided doses. For example, the composition may be administered two or more times separated by 4 hours, 6 hours, 8 hours, 12 hours, a day, two days, three days, four days, one week, two weeks, or by three or more weeks.

An effective amount or a therapeutically effective amount as used herein means the amount of a composition that, when administered to a subject for treating a state, disorder or condition is sufficient to effect a treatment (as defined above). The therapeutically effective amount will vary depending on the composition, formulation or composition, the disease and its severity and the age, weight, physical condition and responsiveness of the subject to be treated.

The following examples are meant only to be illustrative and are not meant as limitations on the scope of the invention or of the appended claims. All references cited herein are hereby incorporated by reference in their entireties.

EXAMPLES

The peptoids described herein are generated using the methods described in Zuckermann, R. N., J. M. Kerr, S. B. H. Kent, and W. H. Moos, *Efficient method for the preparation of peptoids [oligo(N-substituted glycines)] by submonomer solid-phase synthesis.* J. Am. Chem. Soc., 1992. 114 (26): p. 10646-7 which is incorporated herein by reference in its entirety and is shown below. Briefly, peptoids are synthesized using an ABI 433A automated peptide synthesizer on Rink amide resin following a submonomer protocol, with Boc protection of the NLys side chain. Peptoid oligomers are cleaved from the resin with a mixture of 95% TFA/water along with necessary protecting group scavengers. Peptoids are purified by RP-HPLC using a linear gradient of 0.1% TFA in water [v/v] and 0.1% TFA in acetonitrile [v/v]. Final purities of the peptoids are confirmed to be >97% by analytical RP-HPLC and molecular weights are confirmed by MALDI mass spectrometry.

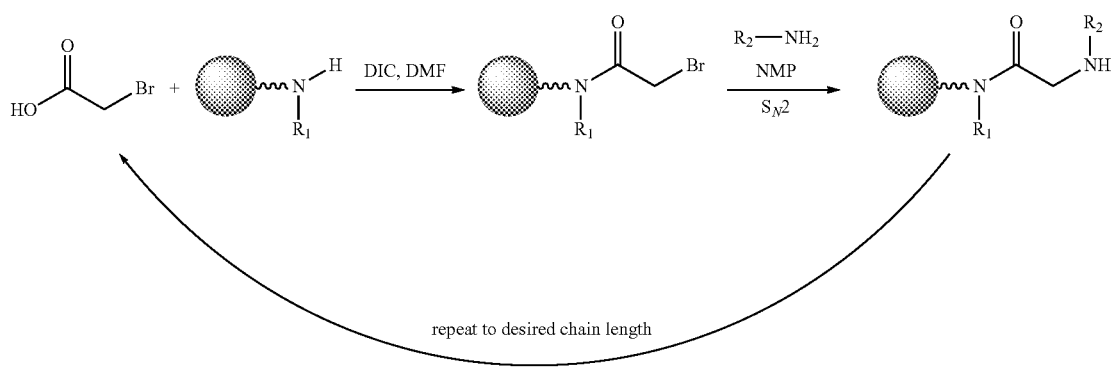

Figure 2:
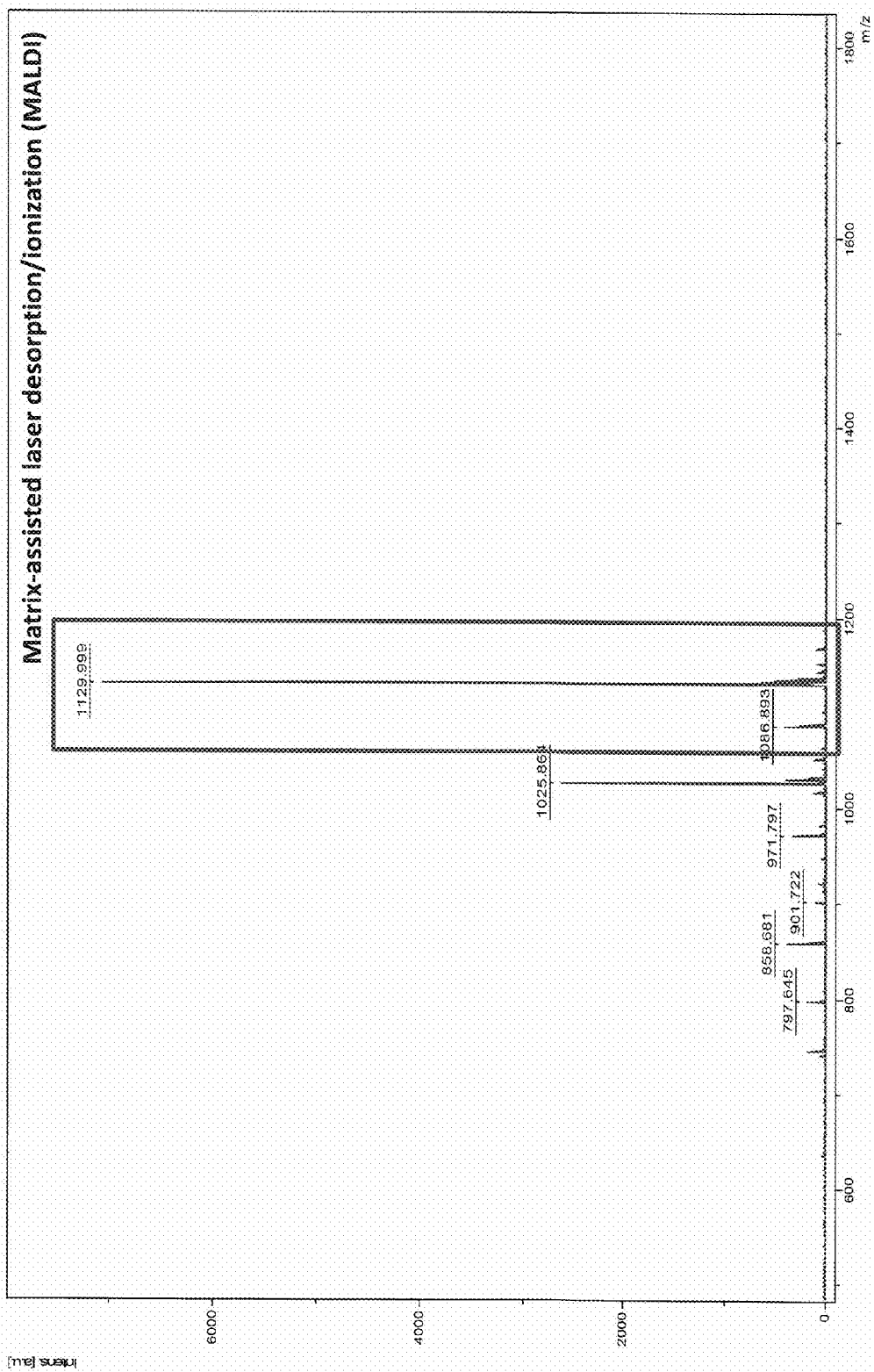
FIG. 2 is a graph showing the mass of the synthesized peptoid 1 as measured by MALDI.
Figure 3:
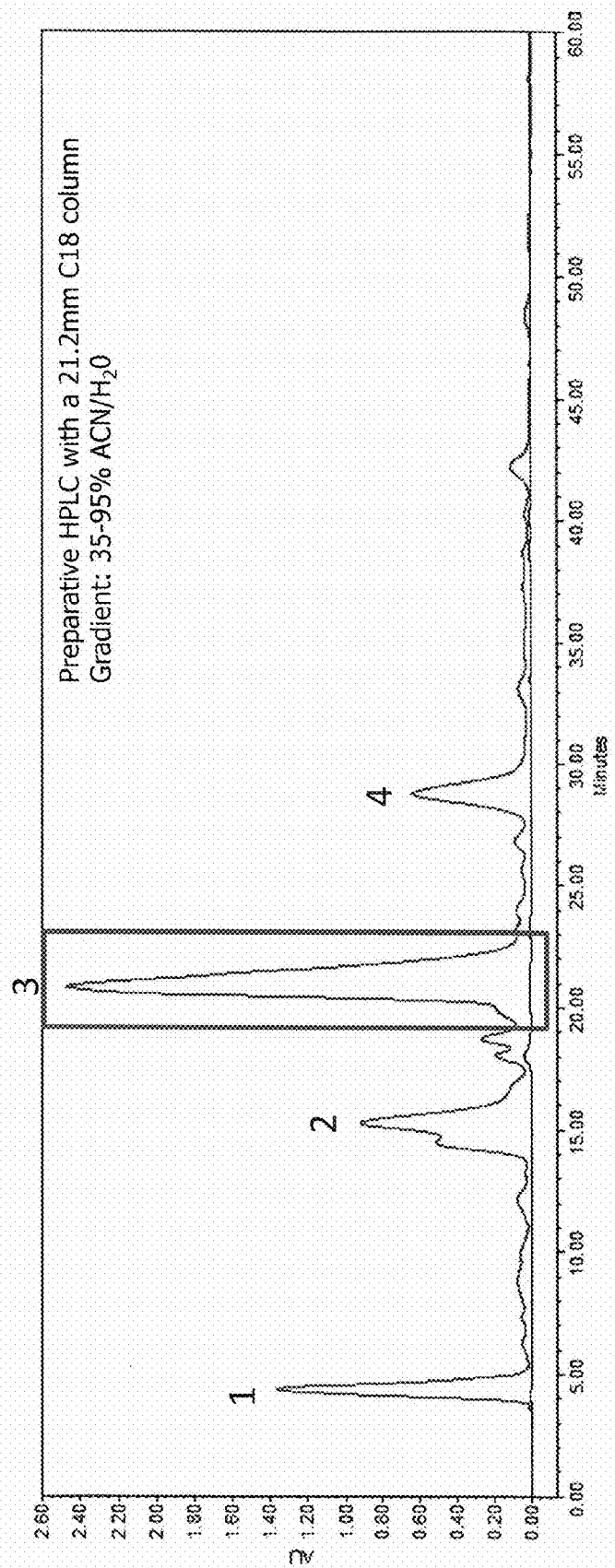
FIG. 3 is a graph showing the preparative HPLC tracing of peptoid 1.
Figure 4:
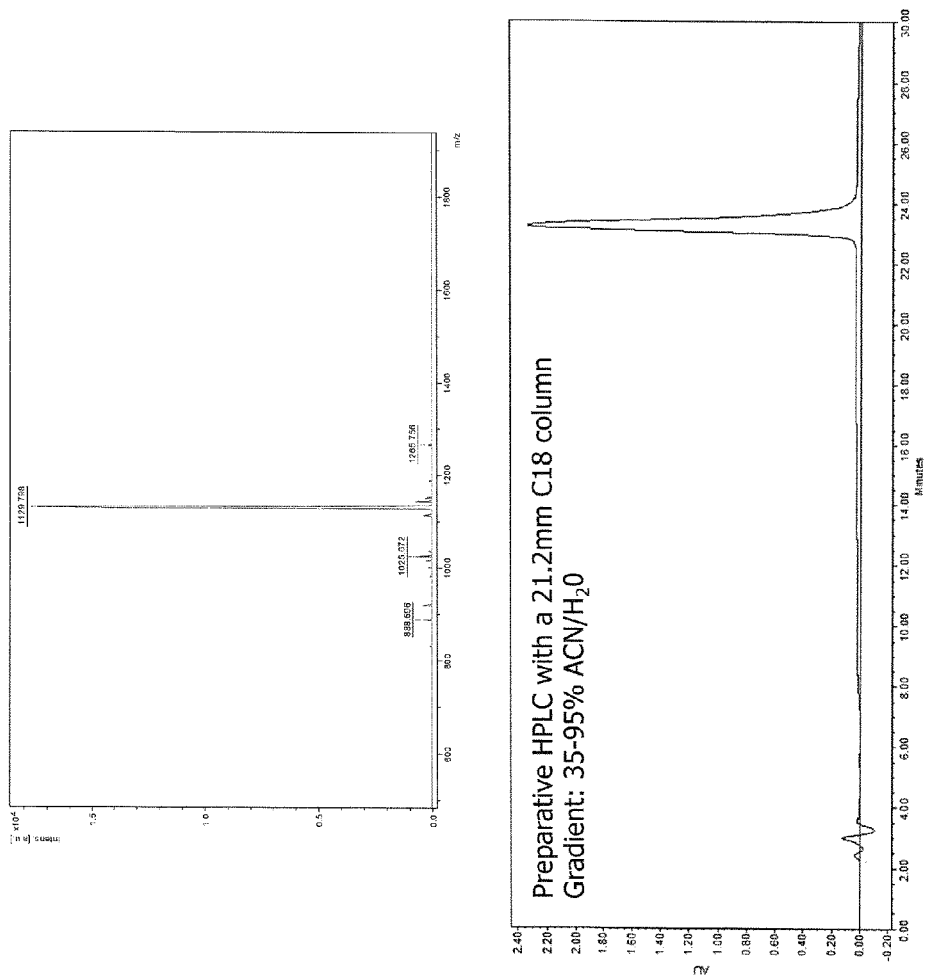
FIG. 4 is a set of graphs showing the MALDI and analytical HPLC of the purified peptoid 1.
Figure 5:
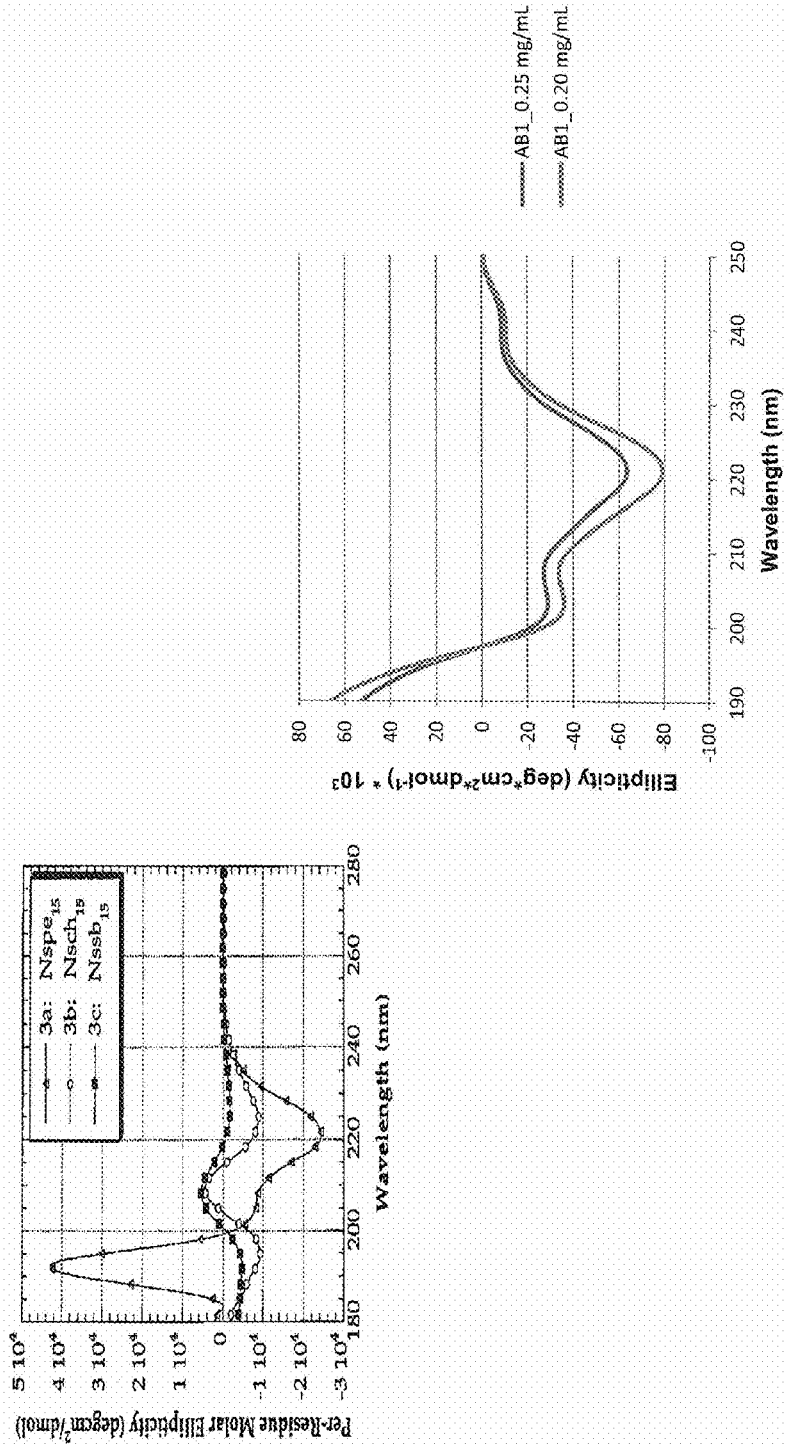
FIG. 5 is a set of graphs showing a typical helical peptoid structure on the left and the structure of peptoid 1.

The peptoids shown in FIG. 1 were synthesized. Peptoid 1 was synthesized first and its mass was confirmed using Matrix-assisted laser desorption/ionization (MALDI) as shown in FIG. 2. The peptoid was then purified using preparative HPLC with a 21.2 mm C18 column and a gradient of 35-95% acetonitrile/water as shown in FIG. 3. The purified peptoid 1 was confirmed by MALDI and analytical HPLC under similar conditions and is shown in FIG. 4. The peptoid was shown to have a helical structure in FIG. 5 by the method of Patch et al. (N-substituted) glycines: The many roles of peptoids in drug discovery; Pseudo-Peptides in Drug Discovery; Wiley-VCG Verlag 2004, which is incorporated herein by reference in its entirety. Thus the synthesized peptoid 1 has the predicted structure. Peptoids 2 and 3 shown in FIG. 1 have been synthesized using similar methods and their structure has also been confirmed.

The peptoid was then used in a Thioflavin T (ThT) assay to assess the ability of the peptide to inhibit the growth of $A\beta$ aggregates. The method used was that of Soto-Ortega et al., Inhibition of amyloid-$\beta$ aggregation by coumarin analogs can be manipulated by functionalization of the aromatic center, Bioorg Med Chem 19: 2596-2602 (2011), which is incorporated herein by reference in its entirety. Briefly, aliquots of $A\beta(1-40)$ monomer, purified via size exclusion chromatography on Superdex 75, were prepared at a concentration of 20 μM in 40 mM Tris-HCl (pH 8.0) containing 150 mM NaCl and incubated under agitation (vortexing, 500-800 rpm) at 25° C. in the absence or presence of the indicated concentration of the peptoid. Periodically, a 20 μl aliquot was removed and diluted into 10 μM ThT in a final volume of 140 μl. Fluorescence was measured at an excitation of 450 nm and an emission of 470-500 nm, with the fluorescence determined as the area under the emission peak with baseline (ThT) subtraction.

Figure 6:
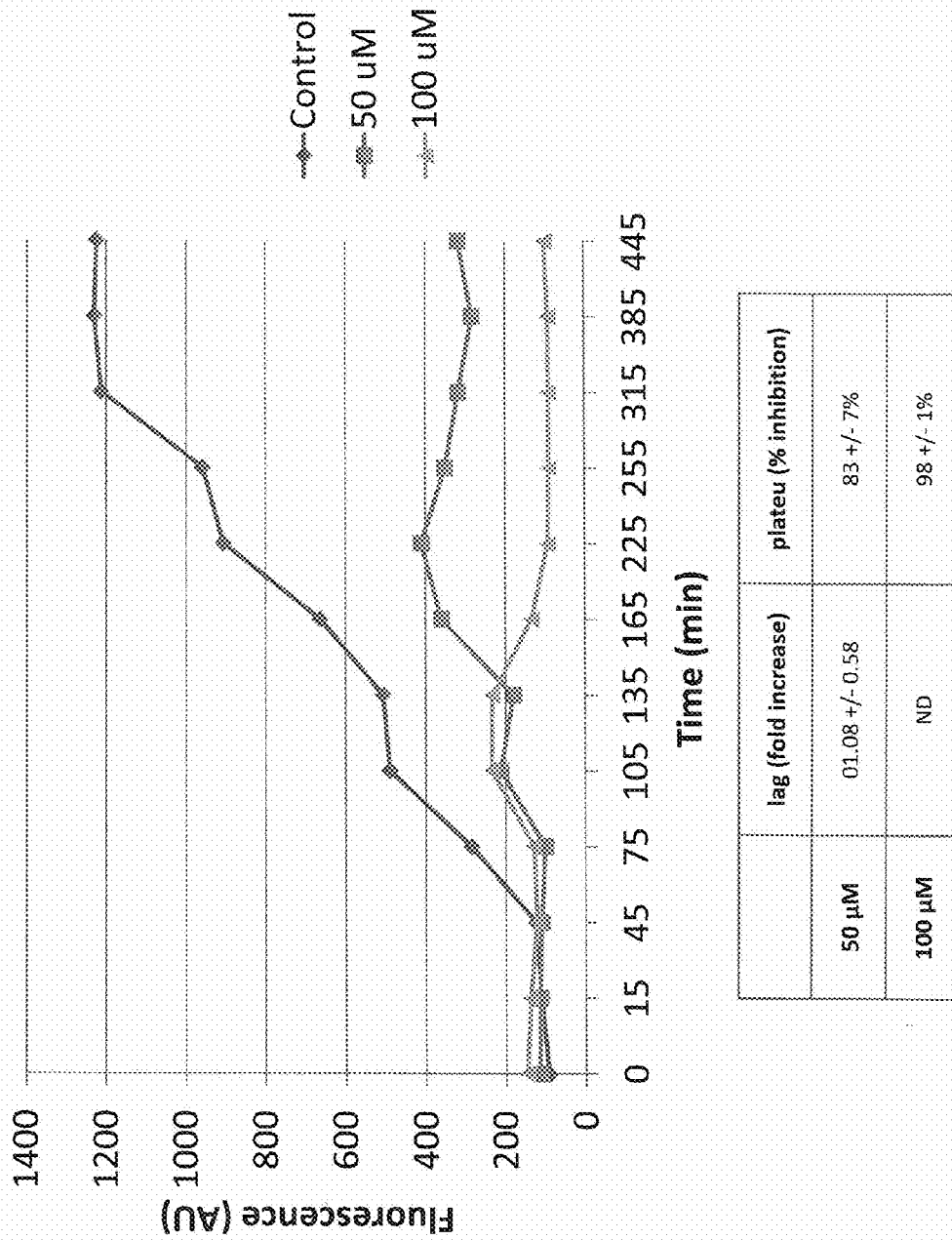
FIG. 6 is a graph showing the results of the thioflavin T assay demonstrating that peptoid 1 is capable of inhibiting Aβ aggregation in vitro.

The results for peptoid 1 in the ThT assay are shown in FIG. 6. At 100 μM, the peptoid was able to inhibit 98% of the aggregation in the assay. This represents a 5 to 1 ratio of peptoid to $A\beta$. At 50 μM, the peptoid was able to inhibit 83% of the aggregation in the assay. This represents a 10 to 1 ratio of the peptoid to the $A\beta$. FIG. 7 shows the results using the ThT assay with decreasing amounts of peptoid 1 and peptoid 3. The only difference between peptoid 1 and peptoid 3 is in the side chain of the 6$^{th}$ monomer. Peptoid 1 has a neutral side chain, while peptoid 3 has a negatively charged side chain. As measured by a two way analysis of variance with the Bonferroni means comparison test, Peptoid 1 is significantly better at inhibiting aggregation of $A\beta$ at 20-100 μM of the peptoid at the base time point. Peptoid 1 was also capable of significantly inhibiting $A\beta$ aggregation at 50 and 100 βM after 2 hours of further incubation. Notably, peptoid 1 was better at inhibiting $A\beta$ aggregation than peptoid 3, but peptoid 3 was able to significantly inhibit aggregation at least at 100 βM at the minimal incubation time point.

The results of the ThT assay were confirmed using a dot blot assay with antibodies capable of binding to $A\beta$ fibrils, but not $A\beta$ monomers or pre-fibrils (LOC, available from Millipore). Thus, reduction of signal in the dot blot as compared to control is indicative of the peptoid blocking fibril formation. The intensity of the dot blot signal detecting the binding of the LOC antibody to the $A\beta$ fibrils after incubation with a control was set to 100% to indicate maximal fibril formation. This can then be compared to the intensity of the LOC antibody dot blot signal after incubation of the $A\beta$ with each of the peptoids. A reduction in the percent of antibody binding is indicative of inhibition of aggregation of $A\beta$ in the assay. As can be seen in Table 1 below, after minimal incubation all three peptoids were capable of inhibiting $A\beta$ aggregation to at least some extent. To control for the signal being at the maximum intensity parallel samples were diluted in half with 40 mM Tris buffer before being blotted (1:2). After 2 hours of incubation, none of the peptoids were capable of inhibiting aggregation of $A\beta$ at a 1:1 dilution, likely because the antibody signal is too saturated to detect any effect of the peptoids. All three peptoids were able to inhibit aggregation to a significant degree at the 1:2 dilution, but peptoid 1 appear to perform better than either peptoid 2 or 3 in this assay.

TABLE 1

| Time (hr) | Dilution | Control (%) | Peptoid 1 (%) | Peptoid 2 (%) | Peptoid 3 (%) |
|---|---|---|---|---|---|
| 0 | 1:1 | 100 | 79.58 | 73.03 | 70.60 |
| 0 | 1:2 | 100 | 68.41 | 56.91 | 94.40 |
| 2 | 1:1 | 100 | 98.95 | 108.61 | 106.62 |
| 2 | 1:2 | 100 | 66.97 | 89.63 | 77.36 |

The data demonstrate that the peptoids are capable of inhibiting or at least slowing the aggregation of $A\beta$ into fibrils in vitro. We expect similar inhibition of the $A\beta$ plaque formation by the peptoids when used in vivo to slow the progression of AD.

We claim:

1. A method of using a pharmaceutical composition to inhibit amyloid β aggregation or to slow the progression of Alzheimer's disease comprising administering the composition to a subject in need of inhibition of amyloid β aggregation, wherein the pharmaceutical composition comprises a peptoid and a pharmaceutically acceptable carrier, the peptoid having the following formula: $X-(-NR_a-CH_2-CO-)_b-Y$ wherein b is an integer between 8 and 35,
wherein a is an integer between 1 and b and each consecutive a representing the R in each consecutive monomer,
wherein X is H,
wherein Y is selected from $NH_2$, H and OH,
wherein $R_1$ and $R_6$ of the peptoid are independently either an unbranched, saturated or unsaturated, $C_1$-$C_{10}$ alkyl group substituted with a nitrogen and lacking a chiral center or a unbranched, unsubstituted, saturated or unsaturated $C_1$-$C_{10}$ alkyl group having an (S) chiral center;
wherein $R_2$ and $R_3$ are unbranched. unsubstituted $C_1$-$C_{10}$ alkyl groups with an (S) chiral center or lacking a chiral center
wherein at least $R_4$, $R_5$, $R_7$ and $R_8$ of the peptoid comprise a branched or unbranched, substituted or unsubstituted arylalkyl group with an (S) chiral center,
wherein the remaining R groups are branched or unbranched, substituted or unsubstituted, saturated or unsaturated, $C_1$-$C_{10}$ alky, $C_4$-$C_{10}$ aryl, or $C_4$-$C_{10}$ cycloalkyl groups,
wherein the peptoid forms a helical structure with three monomers per such that the R groups comprising the arylalkyl groups are positioned on the same face of the peptoid, and
wherein the R groups with chiral centers have an (S) chiral center.

2. The method of claim 1, wherein the peptoid has a structure selected from the group consisting of peptoid 1 and peptoid 2, as shown below:

3. The method of claim 1, wherein b is less than 25.

4. The method of claim 1, wherein at least four of the R groups are branched arylalkyl groups with (S) chiral centers.

5. The method of claim 1, Wherein administration of the pharmaceutical composition slows progression of Alzheimer's disease as compared to treatment with a control composition or no treatment.

6. The method of claim 1, further comprising administering a second composition capable of slowing the progression of Alzheimer's disease.

7. The method of claim 6, wherein the pharmaceutical composition is administered before, after or concomitantly with the second composition.

8. The method of claim 1, wherein administration inhibits aggregation of Amyloid β by at least 20% as compared to an untreated subject.

9. The method of claim 1, wherein the administration slows progression of Alzheimer's disease related dementia by at least 10% as compared to untreated subjects.

10. The method of claim 1, wherein b is 8.

11. The method of claim 1, wherein at least $R_4$, $R_5$, $R_7$ and $R_8$ are (S)—N—(1—phenylethyl).

12. The method of claim 1, wherein $R_1$ is a $C_2$-$C_5$ aminoalkyl.

* * * * *

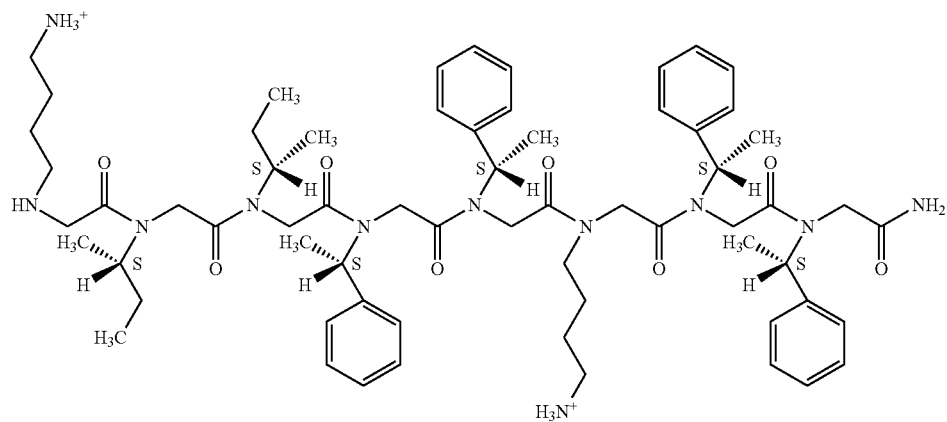

Peptoid 1

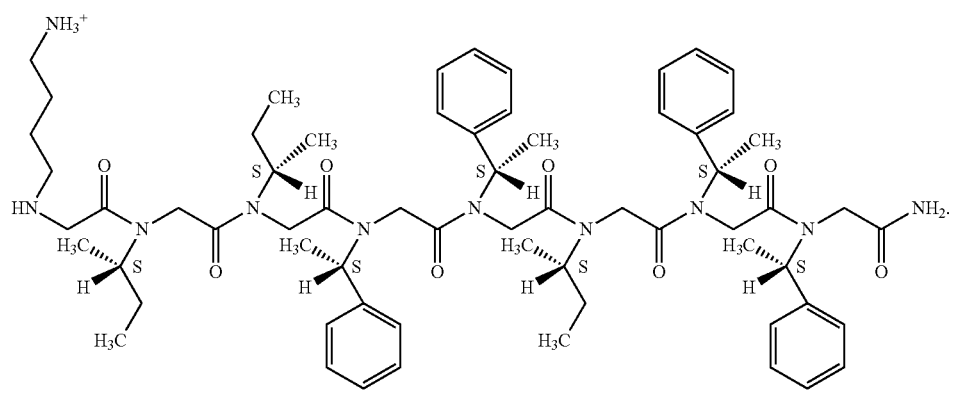

Peptoid 2